(12) United States Patent
Haag et al.

(10) Patent No.: US 7,906,678 B2
(45) Date of Patent: Mar. 15, 2011

(54) CRYSTALLINE POTASSIUM SALT OF LIPOXIN A4 ANALOGS

(75) Inventors: Tilo Haag, Berlin (DE); Danja Grossbach, Berlin (DE); Gabriele Winter, Schönfliess (DE); Michael Sander, Frechen (DE); Wolfgang Beckmann, Berlin (DE); Klaus Bartel, Berlin (DE); Christian Dinter, Berlin (DE)

(73) Assignee: Bayer Schering Pharma Aktiengesellschaft, Berlin (DE)

(*) Notice: Subject to any disclaimer, the term of this patent is extended or adjusted under 35 U.S.C. 154(b) by 233 days.

(21) Appl. No.: 11/999,000

(22) Filed: Dec. 3, 2007

(65) Prior Publication Data
US 2008/0182897 A1    Jul. 31, 2008

Related U.S. Application Data

(60) Provisional application No. 60/872,830, filed on Dec. 4, 2006.

(51) Int. Cl.
C07C 59/00    (2006.01)

(52) U.S. Cl. ........................................ 562/471; 562/472

(58) Field of Classification Search .................. None
See application file for complete search history.

(56) References Cited

U.S. PATENT DOCUMENTS

| | | | |
|---|---|---|---|
| 5,441,951 | A | 8/1995 | Serhan |
| 6,066,466 | A | 5/2000 | Serhan et al. |
| 6,100,296 | A | 8/2000 | Madara et al. |
| 6,831,186 | B2 | 12/2004 | Bauman et al. |
| 7,223,798 | B2 | 5/2007 | Bauman et al. |
| 2004/0162433 | A1 | 8/2004 | Bauman et al. |

FOREIGN PATENT DOCUMENTS

| | | |
|---|---|---|
| WO | WO 94/29262 | 12/1994 |
| WO | WO 95/01179 | 1/1995 |
| WO | WO 98/11049 | 3/1998 |
| WO | WO 00/44744 | 8/2000 |
| WO | WO 00/54761 | 9/2000 |
| WO | WO 00/54767 | 9/2000 |
| WO | WO 00/55109 | 9/2000 |
| WO | WO 01/34144 | 5/2001 |
| WO | WO 01/70664 | 9/2001 |
| WO | WO 03/050124 | 6/2003 |
| WO | WO 03/078425 | 9/2003 |
| WO | WO 2004/066997 | 8/2004 |
| WO | WO 2006/035291 | 4/2006 |
| WO | WO 2007/053724 | 5/2007 |

OTHER PUBLICATIONS

Fiorucci et al, PNAS, 2004, vol. 101, No. 44, pp. 15736-15741.*
Leonard, M. O. et al., "15-Epi-16-(Para-Fluorophenoxy)-Lipoxin A4(the 4 needs to be subscript)-Methyl Ester, a Synthetic Analougue of 15-epi-Lipoxin A4(the 4 needs to be subscript), Is Protectice in Experimental Ischemic Acute Renal Failure," J. Am. Soc. Nephrol, 2002, vol. 13, No. 6, pp. 1657-1662.

* cited by examiner

*Primary Examiner* — Sudhakar Katakam
(74) *Attorney, Agent, or Firm* — Millen, White, Zelano & Branigan, P.C.

(57) ABSTRACT

This invention is directed to the crystalline potassium salt of a lipoxin $A_4$ analog of Formula (I):

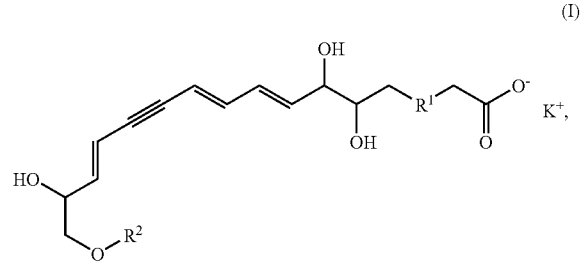

processes for preparing the crystalline potassium salts, methods for using them to treat disease-states characterized by inflammation, and pharmaceutical compositions comprising such crystalline potassium salts.

10 Claims, 3 Drawing Sheets

CRYSTALLINE POTASSIUM SALT OF LIPOXIN A4 ANALOGS

This application claims the benefit of Provisional U.S. application Ser. No. 60/872,830, filed Dec. 4, 2006, the entire disclosure of which is incorporated herein by reference.

The invention relates to the crystalline potassium salts of lipoxin $A_4$ analogs, their use in treating a disease-state characterized by inflammation, and pharmaceutical compositions containing the crystalline potassium salts of the analogs and processes for their preparation.

Lipoxins, together with leukotrienes, prostaglandins, and thromboxanes, constitute a group of biologically active oxygenated fatty acids collectively referred to as the eicosanoids. Eicosanoids are all synthesized de novo from membrane phospholipid via the arachidonic acid cascade of enzymes. Since their initial discovery in 1984, it has become apparent that lipoxins, which are a structurally unique class of eicosanoids, possess potent anti-inflammatory properties that suggest they may have therapeutic potential (Serhan, C. N., *Prostaglandins* (1997), Vol. 53, pp. 107-137; O'Meara, Y. M. et al., *Kidney Int.* (Suppl.) (1997), Vol. 58, pp. S56-S61; Brady, H. R. et al., *Curr. Opin. Nephrol. Hypertens.* (1996), Vol. 5, pp. 20-27; and Serhan, C. N., *Biochem. Biophys. Acta.* (1994), Vol. 1212, pp. 1-25). Of particular interest is the ability of lipoxins to antagonize the pro-inflammatory functions of leukotrienes in addition to other inflammatory agents such as platelet activating factor, fMLP (formyl-Met-Leu-Phe) peptide, immune complexes, and TNFα. Lipoxins are thus potent anti-neutrophil agents which inhibit polymorphoneutrophil (PMN) chemotaxis, homotypic aggregation, adhesion, migration across endothelial and epithelial cells, margination/diapedesis and tissue infiltration (Lee, T. H., et al., *Clin. Sci.* (1989), Vol. 77, pp. 195-203; Fiore, S., et al., *Biochemistry* (1995), Vol. 34, pp. 16678-16686; Papyianni, A., et al., *J. Immunol.* (1996), Vol. 56, pp. 2264-2272; Hedqvist, P., et al., *Acta. Physiol. Scand.* (1989), Vol. 137, pp. 157-572; Papyianni, A., et al., *Kidney Intl.* (1995), Vol. 47, pp. 1295-1302). In addition, lipoxins are able to down-regulate endothelial P-selectin expression and adhesiveness for PMNs (Papyianni, A., et al., *J. Immunol.* (1996), Vol. 56, pp. 2264-2272), bronchial and vascular smooth muscle contraction, mesangial cell contraction and adhesiveness (Dahlen, S. E., et al., *Adv. Exp. Med. Biol.* (1988), Vo. 229, pp. 107-130; Christie, P. E., et al., *Am. Rev. Respir. Dis.* (1992), Vol. 145, pp. 1281-1284; Badr, K. F., et al., *Proc. Natl. Acad. Sci.* (1989), Vol. 86, pp. 3438-3442; and Brady, H. R., et al., *Am. J. Physiol.* (1990), Vol. 259, pp. F809-F815) and eosinophil chemotaxis and degranulation (Soyombo, O., et al., *Allergy* (1994), Vol. 49, pp. 230-234).

This unique anti-inflammatory profile of lipoxins, particularly lipoxin $A_4$, has prompted interest in exploiting their potential as therapeutics for the treatment of inflammatory or autoimmune disorders and pulmonary and respiratory tract inflammation. Such disorders and inflammations that exhibit a pronounced inflammatory infiltrate are of particular interest and include, but are not limited to, inflammatory bowel diseases such as Crohn's disease, dermatologic diseases such as psoriasis, rheumatoid arthritis, and respiratory disorders, such as asthma.

As with other endogenous eicosanoids, naturally-occurring lipoxins are unstable products that are rapidly metabolized and inactivated (Serhan, C. N., *Prostaglandins* (1997), Vol. 53, pp. 107-137). This has limited the development of the lipoxin field of research, particularly with respect to in vivo pharmacological assessment of the anti-inflammatory profile of lipoxins. Several U.S. Patents have been issued directed to compounds having the active site of lipoxin $A_4$, but with a longer tissue half-life. See, e.g., U.S. Pat. Nos. 5,441,951 and 5,648,512. These compounds retain lipoxin $A_4$ receptor binding activity and the potent in vitro and in vivo anti-inflammatory properties of natural lipoxins (Takano, T., et al., *J. Clin. Invest.* (1998), Vol. 101, pp. 819-826; Scalia, R., et al., *Proc. Natl. Acad. Sci.* (1997), Vol. 94, pp. 9967-9972; Takano, T., et al., *J. Exp. Med.* (1997), Vol. 185, pp. 1693-1704; Maddox, J. F., et al., *J. Biol. Chem.* (1997), Vol. 272, pp. 6972-6978; Serhan, C. N., et al., *Biochemistry* (1995), Vol. 34, pp. 14609-14615).

Lipoxin $A_4$ analogs of interest to the invention are disclosed in U.S. Pat. No. 6,831,186 and in U.S. Patent Application Publication No. 2004/0162433.

It is recognized in the art that it is particularly advantageous that a solid pharmaceutical substance is crystalline, rather than amorphous. Typically during the formation of a crystalline solid by crystallisation from a solution, a purification of the crystalline product is obtained. A crystalline solid state form can be very well characterized and usually shows a higher stability in comparison to an amorphous phase. By using a crystalline solid as drug substance or ingredient of a drug product, a potential recrystallisation of the amorphous phase, including the change of the characteristics of the drug substance or drug product, is avoided. Accordingly, there exists a need for a stable crystalline solid state form of the lipoxin $A_4$ analogs disclosed in U.S. Pat. No. 6,831,186 and in U.S. Patent Application Publication No. 2004/0162433.

SUMMARY

This invention is directed to a potent, selective, and metabolically and chemically stable crystalline potassium salt of a lipoxin $A_4$ analog and its use in treating disease-states characterized by inflammation, such as inflammatory or autoimmune disorders and pulmonary or respiratory tract inflammation in mammals, particularly in humans.

Accordingly, in one aspect this invention is directed to a crystalline potassium salt of a lipoxin $A_4$ analog of Formula (I):

wherein:

$R^1$ is —O—, —S(O)$_t$— (where t is 0, 1 or 2), or a straight or branched alkylene chain; and $R^2$ is aryl (optionally substituted by one or more substituents selected from alkyl, alkoxy, halo, haloalkyl and haloalkoxy) or aralkyl (optionally substituted by one or more substituents selected from alkyl, alkoxy, halo, haloalkyl and haloalkoxy);

and wherein the compound of Formula (I) is a single stereoisomer or any mixtures of stereoisomers.

The present invention encompasses all of the crystalline forms of the potassium salt of Formula (I).

The salt of the invention exhibits an excellent stability under stress test conditions.

In another aspect, this invention is directed to a method of preparing the crystalline potassium salt of Formula (I), the method comprising i) mixing a potassium base, in a suitable solvent, together with the free acid corresponding to the potassium salt of Formula (I), in a suitable solvent; ii) optionally cooling the resulting suspension; iii) isolating the resulting crystals from the resulting suspension; iv) optionally washing the isolated crystals with a suitable solvent; and v) drying the isolated crystals, to give the crystalline potassium salt.

The method of the invention in one embodiment comprises the preparation of a suitable solution of acid and base, namely the addition of appropriate amounts of water to induce the formation of crystals with a high crystallinity.

The method of the invention in one embodiment comprises the controlled drying of the salt to a desired hydrate state, this state being either dihydrate, monohydrate or the dehydrated state.

The method of the invention in one embodiment is directed to the preparation of the crystalline anhydrate form of the potassium salt of Formula (I), the method comprising digestion of a hydrate or mixture of hydrates of the potassium salt (I) in a suitable solvent.

In a further aspect, this invention is directed to pharmaceutical compositions comprising a therapeutically effective amount of a crystalline potassium salt of Formula (I), as described above, and one or more pharmaceutically acceptable excipients.

In another aspect, this invention is directed to the use of a crystalline potassium salt of Formula (I), as described above, for the manufacture of a medicament for treating a mammal having a disease-state characterized by inflammation, such as for example an inflammatory or autoimmune disorder or a pulmonary or respiratory tract inflammation.

In another aspect, this invention is directed to methods of treating a disease-state in a mammal, particularly a human, characterized by inflammation, wherein the method comprises administering to the mammal in need thereof a therapeutically effective amount of a crystalline potassium salt of Formula (I) as described above. The disease-state may be, for example, an inflammatory or autoimmune disorder or a pulmonary or respiratory tract inflammation.

A. DEFINITIONS

All of the references cited herein, including U.S. patents, U.S. published patent applications and journal articles, are incorporated in full by reference herein.

As used herein the singular forms "a", "an", and "the" include plural referents unless the context clearly dictates otherwise. For example, "a compound" refers to one or more of such compounds, while "the enzyme" includes a particular enzyme as well as other family members and equivalents thereof as known to those skilled in the art.

All percentages herein are by volume, unless otherwise indicated.

Furthermore, as used in the specification and appended claims, unless specified to the contrary, the following terms have the meaning indicated:

"Alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl(isopropyl), n-butyl, n-pentyl, 1,1-dimethylethyl(t-butyl), and the like.

"Alkylene chain" refers to a straight or branched divalent hydrocarbon chain consisting solely of carbon and hydrogen, containing no unsaturation and having from one to eight carbon atoms, e.g., methylene, ethylene, propylene, n-butylene, and the like.

"Alkoxy" refers to a radical of the formula —OR$_a$ where R$_a$ is an alkyl radical as defined above.

"Aryl" refers to a phenyl or naphthyl radical. Unless stated otherwise, the aryl radical may be optionally substituted by one or more substituents selected from the group consisting of alkyl, alkoy, halo, haloalkyl or haloalkoxy. Unless stated otherwise specifically in the specification, it is understood that such substitution can occur on any carbon of the aryl radical.

"Aralkyl" refers to a radical of the formula —R$_a$R$_b$ where R$_a$ is an alkyl radical as defined above and R$_b$ is an aryl radical as defined above, e.g., benzyl and the like. The aryl radical may be optionally substituted as described above.

"Halo" refers to bromo, chloro, iodo or fluoro.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl (1,3-difluoroisopropyl), 3-bromo-2-fluoropropyl, 1-bromomethyl-2-bromoethyl (1,3-dibromoisopropyl), and the like.

"Haloalkoxy" refers to a radical of the formula —OR$_c$ where R$_c$ is an haloalkyl radical as defined above, e.g., trifluoromethoxy, difluoromethoxy, trichloromethoxy, 2,2,2-trifluoroethoxy, 1-fluoromethyl-2-fluoroethoxy, 3-bromo-2-fluoropropoxy, 1-bromomethyl-2-bromoethoxy, and the like.

As used herein, compounds which are "commercially available" may be obtained from standard chemical supply houses and other commercial sources including, but not limited to, Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.) Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

"Mammal" includes humans and domesticated animals, such as cats, dogs, swine, cattle, sheep, goats, horses, rabbits, and the like.

As used herein, "methods known to one of ordinary skill in the art" may be identified though various reference books and databases. Suitable reference books and treatises that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A.

Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses (such as, for example, those listed above) provide custom synthesis services.

"Optional" or "optionally" or "may be" means that the subsequently described event or circumstance may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Polymorphs" refers to crystalline states of the same chemical compounds of the invention. Wherein the "chemical compounds" involves molecules or ions (salt) or a mixtures of a molecule and an ion (salt). Solids exist in either amorphous or crystalline forms. In the case of crystalline forms, molecules are systematically positioned in 3-dimensional lattice sites. When a compound crystallizes from a solution or slurry, it may crystallize with different spatial lattice arrangements, a property referred to as "polymorphism," with the different crystal forms individually being referred to as a "polymorph". Different polymorphic forms of a given substance may differ from each other with respect to one or more physical properties, such as solubility and dissolution, true density, crystal shape, compaction behavior, flow properties, and/or solid state stability. In the case of a chemical substance that exists in two (or more) polymorphic forms, the unstable forms generally convert to the more thermodynamically stable forms at a given temperature after a sufficient period of time. The thermodynamically unstable form is referred to as the "metastable" form. The transformation to a more stable form can be slow enough as to assess the properties of the form even for drug substance use. Thus, the metastable form may be found to exhibit sufficient chemical and physical stability under normal storage conditions as to permit its use in a commercial form. In this case, the metastable form, although less stable, may exhibit properties desirable over those of the stable form, such as enhanced solubility or better oral bioavailability.

"Solvate" refers to an aggregate that comprises one or more molecules of a compound of the invention with one or more molecules of solvent or a non stoichiometric content of a solvent. The solvent may be water, in which case the solvate is called a hydrate. Alternatively, the solvent may be an organic solvent. Thus, the potassium salts of lipoxin $A_4$ analogs of Formula (I) may exist as a hydrate, including a monohydrate, dihydrate, hemihydrate, sesquihydrate, trihydrate, tetrahydrate, the dehydrated hydrates with their non-stoichiometric water content, and the like, as well as the corresponding solvated forms. The potassium salts of Formula (I) may be true solvates, while in other cases the salts may merely retain adventitious water or be a mixture of water plus some adventitious solvent.

See, e.g., Byrn, S et al. "Solid State Chemistry of Drugs", SSCI (1999), for a discussion of polymorphs and solvates, their characterization and properties, and relevance for drug substances and drug products; and Stahl, P and Wermuth, C "Handbook of Pharmaceutical Salts", Wiley (2002), for a discussion of salts, their preparation and properties.

As used herein, "suitable conditions" for carrying out a synthetic step are explicitly provided herein or may be discerned by reference to publications directed to methods used in synthetic organic chemistry. The reference books and treatises set forth above that detail the synthesis of reactants useful in the preparation of compounds of the present invention, will also provide suitable conditions for carrying out a synthetic step according to the present invention.

"Suitable solvent" refers to any solvent that is compatible with the components of the reaction and the reaction conditions. The term encompasses one solvent or a mixture of solvents and includes, but is not limited to organic solvents and water. Suitable solvents are known to those of skill in the art or may be discerned by reference to publications directed to methods used in synthetic organic chemistry.

"Therapeutically effective amount" refers to that amount of a potassium salt of the invention which, when administered to a mammal, particularly a human, in need thereof, is sufficient to effect treatment, as defined below, for a disease-state characterized by inflammation. The amount of a potassium salt of the invention which constitutes a "therapeutically effective amount" will vary depending on the salt, its solvated form, the disease-state to be treated and its severity, the age of the mammal to be treated, and the like, but can be determined routinely by one of ordinary skill in the art.

"Treating" or "treatment" as used herein covers the treatment of a disease-state characterized by inflammation in a mammal, preferably a human, such as for example an inflammatory or autoimmune disorder or a pulmonary or respiratory tract inflammation, and includes:

(i) preventing the disorder or inflammation from occurring in a mammal, in particular, when such mammal is predisposed to the disorder but has not yet been diagnosed as having it;

(ii) inhibiting the disorder or inflammation, i.e., arresting its development; or (iii) relieving the disorder or inflammation, i.e., causing regression of the disorder or inflammation.

The potassium salts of Formula (I) have three asymmetric centers, which give rise to enantiomers, diastereomers, and other stereoisomeric forms that may be defined, in terms of absolute stereochemistry, as (R)- or (S)- or as (D)- or (L)-. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. The compounds described herein contain olefinic double bonds or other centers of geometric asymmetry and, unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

B. CRYSTALLINE POTASSIUM SALTS OF THE INVENTION

It is known that the formation of salts can dramatically increase the stability of a pharmaceutical agent with respect to its free acid and that the stability of salts differ between different salt-forming agents. It is also known that crystalline salt forms can be more stable than amorphous salt forms.

Accordingly, investigations were conducted with the goal of finding a suitable stable crystalline salt of the acid of Formula (II):

(II)

wherein:
R$^1$ is —O—, —S(O)$_t$— (where t is 0, 1 or 2) or a straight or branched alkylene chain; and
R$^2$ is aryl (optionally substituted by one or more substituents selected from the group consisting of alkyl, alkoxy, halo, haloalkyl and haloalkoxy) or aralkyl (optionally substituted by one or more substituents selected from the group consisting of alkyl, alkoxy, halo, haloalkyl and haloalkoxy);
and wherein the acid of Formula (II) is a single stereoisomer or any mixtures of stereoisomers.

Through salt screening assays using a variety of organic and inorganic cations, it was very surprisingly discovered that the crystalline potassium salt of the acid (IIa)

(IIa)

was substantially more stable than every other salt prepared and was also more stable than acid (IIa) itself.

In one embodiment, the invention is directed to a crystalline potassium salt of Formula (I) as disclosed and defined in the Summary.

In another embodiment, the invention is directed to a crystalline potassium salt of Formula (I) where R$^1$ is —O—, and R$^2$ is phenyl optionally substituted by one or more substituents selected from fluoro, chloro and iodo.

In a further embodiment, the compound of the invention is a crystalline potassium salt of Formula (I) where R$^1$ is —O—, and R$^2$ is 4-fluorophenyl.

In another embodiment, the compound of the invention is selected from the following:
potassium 2-((2S,3R,4E,6E,10E,12S)-13-(4-fluorophenoxy)-2,3,12-trihydroxytrideca-4,6,10-trien-8-ynyloxy)acetate;
potassium 2-((2R,3R,4E,6E,10E,12S)-13-(4-fluorophenoxy)-2,3,12-trihydroxytrideca-4,6,10-trien-8-ynyloxy)acetate;
potassium 2-((2S,3S,4E,6E,10E,12S)-13-(4-fluorophenoxy)-2,3,12-trihydroxytrideca-4,6,10-trien-8-ynyloxy)acetate;
potassium 2-((2R,3S,4E,6E,10E,12S)-13-(4-fluorophenoxy)-2,3,12-trihydroxytrideca-4,6,10-trien-8-ynyloxy)acetate;
potassium 2-((2S,3R,4E,6E,10E,12R)-13-(4-fluorophenoxy)-2,3,12-trihydroxytrideca-4,6,10-trien-8-ynyloxy)acetate;
potassium 2-((2R,3R,4E,6E,10E,12R)-13-(4-fluorophenoxy)-2,3,12-trihydroxytrideca-4,6,10-trien-8-ynyloxy)acetate;
potassium 2-((2S,3S,4E,6E,10E,12R)-13-(4-fluorophenoxy)-2,3,12-trihydroxytrideca-4,6,10-trien-8-ynyloxy)acetate; and
potassium 2-((2R,3S,4E,6E,10E,12R)-13-(4-fluorophenoxy)-2,3,12-trihydroxytrideca-4,6,10-trien-8-ynyloxy)acetate.

In another aspect, the present invention is directed to a crystalline potassium salt wherein the crystalline potassium salt is potassium 2-((2S,3R,4E,6E,10E,12S)-13-(4-fluorophenoxy)-2,3,12-trihydroxytrideca-4,6,10-trien-8-ynyloxy)acetate (Ia):

(Ia)

C. SALT SCREENING

The following describes the salt screening assays in more detail:

Materials:

Many inorganic cations were investigated to determine their ability to form a stable crystalline salt of the acid (IIa), including potassium, sodium, calcium, aluminium, magnesium, lithium, and zinc.

Several organic amines were investigated, including N-methylglucamine, diethanolamine, ethylenediamine, choline, lysine, and arginine.

In addition to the foregoing, it was investigated to form a mixed salt of the acid of Formula (IIa) with polyvalent inorganic cations and organic acids.

Test Parameters:

In general, the salt screening assay included the variability of the following different test parameters:
i) Type of cation-compound utilized (e.g., as carbonates, hydroxides, methylates, ethylates).
ii) Type of solvent utilized.
iii) Specific addition or exclusion of water (to assist the formation of hydrates or anhydrates).
iv) Type of crystallization utilized (cooling crystallization, antisolvent crystallization, or evaporation crystallization, and combinations thereof).
v) Type of screening (manual screening as well as high throughput screening).

Results:

Surprisingly, it was discovered that only in the case of using potassium compounds as the base was the formation of a suspension and the isolation of a crystalline salt of the acid (IIa) possible. The experiments with the other cations yielded solutions without a solid phase, with oily phases, or as amorphous solids. The formation of mixed salts failed, as well. Also, high throughput-screening yielded no further crystalline salts of the acid (IIa).

D. SOLID STATE FORMS OF THE POTASSIUM SALT OF FORMULA (Ia)

The crystalline potassium salt of Formula (Ia) forms three well-defined crystalline forms: an anhydrate and two hydrates. In addition, two dehydrated hydrate forms (dehydrated form I and dehydrated form II) were obtained, and an amorphous phase was detected in certain studies. No solvates were detected. The present invention encompasses all crystalline forms of the potassium salts of Formulas (I) and (Ia).

The different solid state forms of the potassium salt (Ia) can be differentiated by the peak positions of the reflections in the X-ray powder diffraction (XRPD) pattern. The strongest reflections of anhydrate, monohydrate and dihydrate of crystalline potassium salt (Ia) are given below in Table 1.

TABLE 1

X-ray powder diffraction data of the anhydrate, monohydrate and dihydrate-d-values of the strongest reflections, 2Θ-values (germanium-monochromatized CuKα$_1$-radiation)

| anhydrate d (Å) | monohydrate d (Å) | dihydrate d (Å) |
|---|---|---|
| 26.68 | 26.47 | 27.09 |
| 13.39 | 13.27 | 13.49 |
| 7.24 | 8.44 | 8.49 |
| 4.30 | 5.78 | 5.38 |
| 4.25 | 5.32 | 4.33 |
| 4.10 | 4.32 | 4.16 |
| 3.99 | 4.07 | 4.12 |
| 3.87 | 4.03 | 4.06 |
| 3.69 | 3.98 | 4.00 |
| 3.11 | 3.90 | 3.70 |
|  | 3.81 | 3.66 |
|  | 3.62 | 3.42 |
|  | 3.60 | 3.29 |
|  | 3.20 | 3.24 |

The anhydrate form of the crystalline potassium salt of Formula (Ia) exhibits characteristic peaks at about d=26.7 Å and at about d=3.7 Å.

The monohydrate form of the crystalline potassium salt of Formula (Ia) exhibits characteristic peaks at about d=26.5 Å, at about d=4.3 Å and at about d=4.0 Å, while the dihydrate form of the crystalline potassium salt of Formula (Ia) exhibits characteristic peaks at about d=27.1 Å, at about d=4.2 Å and at about d=4.1 Å.

The XRPD patterns of the dehydrated form I and dehydrated form II of the crystalline potassium salt of Formula (Ia) show that the peak positions for both dehydrated forms vary slightly from batch to batch due to the varying solvent residues. Therefore, no exact d-values, 2Θ-values and relative intensities, which are characteristic for both forms, can be given. However, they exhibit characteristic peaks between about d=24.6 Å and about d=27.1 Å.

One of ordinary skill in the art will appreciate that an X-ray diffraction pattern may be obtained with a measurement error that is dependent upon the measurement conditions employed. In particular, it is generally known that intensities in an X-ray diffraction pattern may fluctuate depending upon crystal habitus of the material and measurement conditions employed. It is further understood that relative intensities may also vary depending upon experimental conditions and, accordingly, the exact order of intensity should not be taken into account. Additionally, a measurement error of diffraction angle Theta for a conventional X-ray diffraction pattern at a given temperature is typically about ±0.1°, and such degree of measurement error should be taken into account as pertaining to the aforementioned diffraction angles. Consequently, the term "about" when used herein in reference to X-ray powder diffraction patterns means that the crystal forms of the instant invention are not limited to the crystal forms that provide X-ray diffraction patterns completely identical to the X-ray diffraction patterns depicted in the accompanying Figure disclosed herein. Any crystal form that provides X-ray diffraction patterns that is substantially identical as to those disclosed in the accompanying Figure falls within the scope of the present invention. The ability to ascertain whether the polymorphic forms of a compound are the same albeit the X-ray diffraction patterns are not completely identical is within the purview of one of ordinary skill in the art.

IR-spectroscopy of the hydrates of the potassium salt (Ia) showed that they have characteristic IR bands at 1214 cm$^{-1}$ and 1127 cm$^{-1}$.

The water content of the crystalline potassium salt (Ia) determines its solid state form (anhydrate, monohydrate, dihydrate, dehydrated form I, or dehydrated form II). The actual water content of the salt is determined by the ambient relative humidity and temperature.

The transformation of the monohydrate and the dihydrate as well as the dehydrated form II into each other is reversible. The anhydrate is transformed into the dihydrate via the monohydrate. This transformation is not reversible. The dihydrate is transformed by dehydration into the dehydrated form II. The dehydrated form I is transformed into the monohydrate and dihydrate as well. No transformation of monohydrate or dihydrate form into the dehydrated form I was observed.

Figure 1:
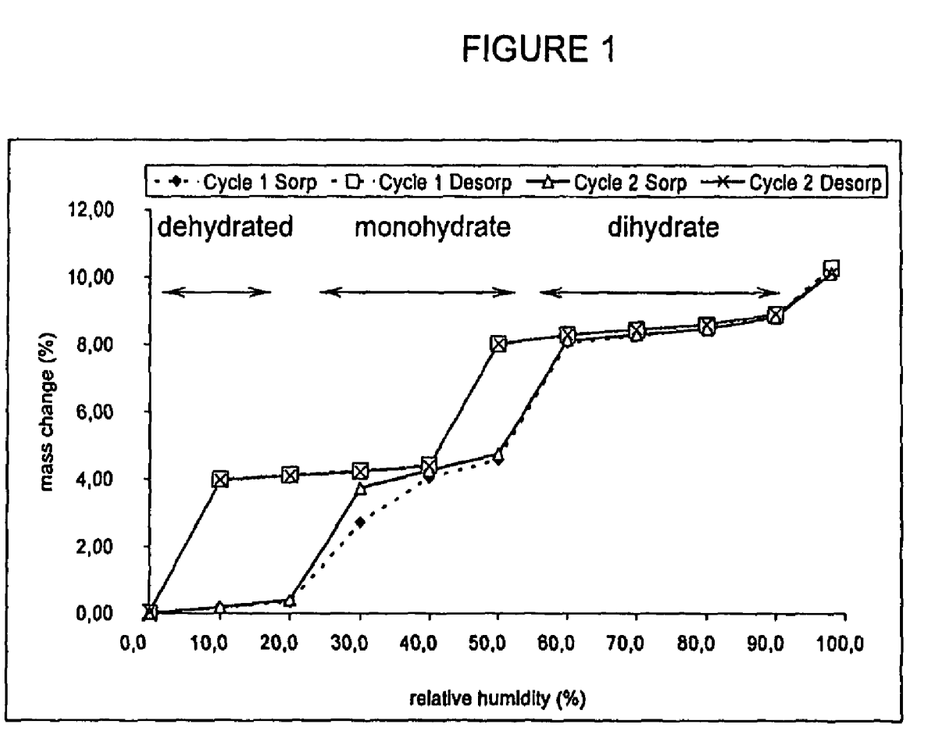
FIG. 1 illustrates a sorption isotherm.

The transformation of the monohydrate to the dihydrate form and vice versa occurs quickly and is well defined at 25° C. and at 40° C. This was shown by dynamic vapor sorption investigations. For example, during pre-drying of the monohydrate at 25° C. and 0% relative humidity, 4.0% water is released from the monohydrate. This results in the formation of dehydrated form II. Between 20% and 40% relative humidity, one mole of water is absorbed, resulting in the formation of the monohydrate. The monohydrate is stable up to approximately 50% relative humidity and then is transformed into the dihydrate by absorption of a second mole of water between 50% and 60% relative humidity. The dihydrate is the stable form up to 98% relative humidity at 25° C. During the desorption cycle between 40% and 50% relative humidity, the transformation into the monohydrate takes place. The formed monohydrate is existent up to 10% relative humidity. Between 0% and 10% relative humidity the dehydration of the monohydrate to the dehydrated form II occurs. The corresponding sorption isotherm is given in FIG. 1. No significant differences between the two cycles were observed.

The hygroscopicity with respect to the transformation of the monohydrate and dihydrate was re-investigated between 45% and 55% relative humidity using smaller steps for the relative humidity. This investigation shows that the equilibrium between the two hydrates at 25° C. is between 48% and 50% relative humidity. At 40° C. the reversible transformation between the monohydrate and the dihydrate is between 57% and 59% relative humidity, approximately 10% higher than at 25° C. A more detailed investigation at 40° C. of the desorption range of the monohydrate between 0% and 10% relative humidity showed that the desorption takes place between 2% and 3% relative humidity.

Also, the transformation of the anhydrate form of the potassium salt (Ia) to the hydrate form was shown by dynamic vapor sorption investigations at 25° C. Up to 40% relative humidity the anhydrate was stable. Between 40% and 60% relative humidity approximately two moles of water are absorbed, resulting in the formation of the dihydrate.

Data collection for the XRPD was carried out in transmission mode using germanium-monochromatized $CuK\alpha_1$-radiation ($\lambda$=1.5406 Å) at room temperature (between 20° C. and 25° C.). The X-ray tube with copper anode was operated by 40 kV and 30 mA. The 2Θ scans were performed using the small linear position sensitive detector with an angular resolution of 0.08° between $3° \leq 2\Theta \leq 35°$ and $2° \leq 2\Theta \leq 35°$ (stepwidth 0.5°) or $7° \leq 2\Theta \leq 35°$ (stepwidth 0.5°) if the wellplate was used. The samples were enclosed between two polyacetate films held together by double-sided adhesive tape or between two aluminum foils to avoid the influence of the humidity during measurement. Data acquisition and evaluation were performed using the STOE WinX$^{pow}$ software package.

The IR spectra were recorded using diffuse reflection technique. The samples were diluted with potassium bromide in a ratio 1:100.

Data collection for the hygroscopicity studies was carried out in an automated water sorption analyzer. Approximately 20 mg of the investigated solid state form of the crystalline potassium salt (Ia) was exposed to a continuous flow of nitrogen with predetermined and constant relative humidity. The rate of sweep gas was set at 200 cm³/min. For a basic assay, two full cycles (sorption/desorption) were measured at 25° C. The measurement was started at 0% relative humidity in order to remove surface water. Once the constant mass was achieved, the next humidity was automatically set. The water sorption/desorption was investigated in steps of 10% between 0% and 90% relative humidity under the criteria for initiation of the first step as set forth herein. Additionally, the sorption at about 98% relative humidity was investigated. Data was acquired using the DVSWin software. In addition, investigations at 40° C. were carried out and, for more detailed evaluation of the monohydrate/dihydrate equilibrium, the steps in the relevant regions were shortened (each step equals 1% relative humidity).

E. CHEMICAL STABILITY OF SOLID STATE FORMS OF THE POTASSIUM SALT (Ia)

The chemical stability of the anhydrate and the monohydrate of the potassium salt of Formula (Ia) of the invention as well as the dehydrated form I of the potassium salt (Ia) of the invention were assessed by comparing the stability under stress at 40° C./75% rH over a period of 4 weeks. The result is shown in the following Table 2.

TABLE 2

|  | K-salt, Anhydrate*; 40° C./ 75% RH | K-salt, Monohydrate**; 40° C./75% RH | K-salt, dehydrated form I; 40° C./75% RH | weeks |
|---|---|---|---|---|
| HPLC- purity [%] | 99.6 | 99.7 | 97.8 | 0 |
|  | 99.7 | 99.6 | 97.1 | 2 |
|  | 99.7 | 99.7 | 95.3 | 4 |

*Started with the anhydrate during the test, it was most likely the dihydrate form of the potassium salt (Ia) at the end of the test
**Started with the monohydrate during the test, it was most likely the dihydrate form of the potassium salt (Ia) at the end of the test All three forms of the potassium salt (Ia) are sufficiently stable; however, the anhydrate and the monohydrate of the potassium salt (Ia) show no sign of degradation.

F. PREPARATION OF THE POTASSIUM SALTS OF FORMULAS (I) AND (Ia)

Compounds of Formula (II), i.e. the acid, are described in detail in U.S. Pat. No. 6,831,186 and in U.S. Patent Application Publication No. 2004/0162433, the pertinent disclosures of which are incorporated in full herein by reference.

The method of preparing the crystalline potassium salt is exemplified by using the salt of Formula (Ia) but can be used to prepare crystalline potassium salts of other compounds of Formula (I). In general, the method of preparing the crystalline potassium salt (Ia) is based on the neutralization of the acid (IIa) by treatment with a base. The resulting mixture forms a suspension, which is then optionally cooled. The crystals are isolated from suspension and dried to yield the desired hydrate form of the crystalline potassium salt (Ia).

More particularly, the acid (IIa) is dissolved in a suitable solvent, such as e.g. ethanol. Then a potassium base, such as potassium methylate or potassium hydroxide for example, is dissolved in a suitable solvent, such as e.g. ethanol. The solution of the potassium base is added to the solution of the acid (IIa) or vice versa.

The dosage of the potassium base to the solution of the acid (III) is controlled by pH-measurement of the resulting mixture by methods known in the art, such as via wet pH-indicator strips. In one embodiment, the addition of the potassium base solution generally is stopped when a pH of 6 to 15 is reached, normally when a pH of 7 to 14 is reached and, in one presently preferred embodiment, when a pH of 8 to 13 is reached.

The dehydrated form I of the potassium salt (Ia) is obtained by excluding water in the reaction mixture. For example, this can be achieved by using water-free solvents and by adding potassium methylate to form the salt.

In addition, the dehydrated form I of the potassium salt (Ia) can be obtained by suspending the monohydrate form of the crystalline potassium salt (Ia) in organic solvents, such as for example acetonitrile. No direct transformation of the monohydrate form or the dihydrate form to the dehydrated form I by drying or thermal treatment is observed.

To avoid the formation of the presently less desired dehydrated hydrate form (I) of the potassium salt (Ia) during the crystallization step, the solvent of the crystallization contains at least some water. Generally, the final reaction mixture contains at least about 0.01% water, normally about 0.5% to about 99.9% water and, in one presently preferred embodiment, about 1% to about 30% water. Thus, for example, in one embodiment, the acid (IIa)-solvent solution will contain at least some water. Generally, the acid (IIa)-solvent solution contains at least about 0.01% water, normally about 0.5% to about 99.9% water and, in one presently preferred embodiment, about 1% to about 30% water. Likewise, in one embodiment, the potassium base-solvent solution will contain at least some water. Generally, the potassium base-solvent solution contains at least about 0.01% water, normally about 0.5% to about 99.9% water and, in one presently preferred embodiment, about 1% to about 30% water. The resulting reaction mixture will contain at least some water. The resulting mixture forms a suspension that is optionally cooled prior to solid/liquid isolation and an optional washing step with a suitable solvent. Generally, the washing solvent contains at least about 0.01% water, normally about 0.5% to about 99.9% water and, in one presently preferred embodiment, about 1% to about 30% water. Then follows the drying step.

The drying procedure of the isolated crystals defines the hydrate form (monohydrate or dihydrate or dehydrated hydrate) of the crystalline potassium salt prepared and thus should be well controlled when one wishes to obtain the desired mono- or dihydrate of the potassium salt (Ia). Also, the drying procedure avoids the formation of the less desired dehydrated form (II) of the potassium salt (Ia, which is obtained by overdrying of the product. The optimization of this process is described in section G below.

The dehydrated form II of the potassium salt (Ia) can also be formed by the dehydration of the hydrates by thermal treatment (normally at a temperature below 100° C.) or by storage at 0% relative humidity. The dehydration of the dihydrate via the monohydrate results in the dehydrated form II.

In general, the method of preparing the anhydrate form of the potassium salt (Ia) is based on the digestion of the hydrate form of the potassium salt in a suitable solvent at higher temperatures for a period of time. The crystals are isolated from suspension and then dried to yield the anhydrate form of the potassium salt (Ia).

More particularly, the hydrate of the potassium salt (Ia) is digested in a suitable solvent, such as e.g. 1,4-dioxane. The suspension is stirred and heated up to nearly the boiling point of the solvent for generally about 0.1 to about 10 hours, normally about 1 to about 8 hours, and preferably about 2 to about 6 hours. Then the suspension is cooled down and the crystals are isolated and optionally washed with a suitable solvent, such as e.g. 1,4-dioxane, after which the crystals are dried to yield the anhydrate form of the potassium salt (Ia).

G. OPTIMIZATION OF THE DRYING PROCESS OF THE POTASSIUM SALT OF FORMULA (Ia)

The formation of the potassium salt (Ia) in a preferred crystalline hydrate form was optimized by varying the drying conditions.

It was found by XRPD analysis of the wet filtercake that the dihydrate form of the potassium salt is formed in the crystallization step. During the drying process the filtercake (that is, the dihydrate form of the potassium salt) loses its moisture. But as the dihydrate form of the potassium salt loses its water and transforms into the monohydrate form, the monohydrate form can subsequently continue to transform to the less desirable dehydrated form II.

As is evident from the DVS data, which shows the dehydrate-monohydrate transition to be fast, a conventional drying process, e.g. via a vacuum drying chamber, will not yield the dihydrate. There is also the potential danger of overdrying of the monohydrate to the dehydrated form II.

Thus, the drying process was optimized to yield either the dihydrate or the monohydrate and to safely avoid overdrying to the dehydrated form II.

The optimized drying process uses a very well-conditioned and controlled sweep gas flow. Through the specific control and setup of relative humidity of the sweep gas (such as, e.g., $N_2$) and of the pressure and the temperature inside the dryer, the drying step was carried out under conditions of temperature and humidity that correlate with the stability domain of the desired hydrate form. Following this process, the specific hydrate forms of the potassium salt (Ia) could be obtained.

Also, investigations revealed that the use of a sweep gas is useful in guaranteeing a sufficient drying time and in avoiding the condensation of liquid in the dryer. In addition to the sweep gas mentioned above, any appropriate sweep gas may be used in the present invention, which gases are known to those of skill in the art or can be determined without undue experimentation.

In addition to the use of a vacuum drying chamber, any drying method or apparatus may be used in the process of the present invention to dry the potassium salts of Formulas (I) and (Ia), including but not limited to a mixing dryer (e.g., paddle dryer or cone dryer), a contact dryer, a convection dryer, a radiation dryer and the like, as are known to or may be identified by those skilled in the art.

H. UTILITY OF THE CRYSTALLINE POTASSIUM SALTS OF THE INVENTION

The crystalline potassium salt of Formula (I) has biological activity similar to that of natural lipoxin $A_4$, but with an enhanced resistance to chemical and metabolic degradation. Accordingly, the crystalline potassium salt of Formula (I) is useful in treating inflammatory or autoimmune disorders in mammals, particularly in humans. In particular, a crystalline potassium salt of Formula (I) is useful in inhibiting acute or chronic inflammation or an inflammatory or autoimmune response that is mediated by neutrophils, eosinophils, T lymphocytes, NK cells or other immune cells that contribute to the pathogenesis of inflammatory, immune or autoimmune diseases. The crystalline potassium salt of Formula (I) is also useful in the treatment of proliferative disorders including, but not limited to, those associated with derangements in the inflammatory or immune response, such as cancer. The crystalline potassium salt of Formula (I) is also useful as an inhibitor of angiogenic responses in the pathogenesis of cancer.

Accordingly, the crystalline potassium salt of Formula (I) can be used to treat the following inflammatory or autoimmune disorders in mammals, particularly in humans: anaphylactic reactions, allergic reactions, allergic contact dermatitis, allergic rhinitis, chemical and non-specific irritant contact dermatitis, urticaria, atopic dermatitis, psoriasis, fistulas associated with Crohn's disease, pouchitis, septic or endotoxic shock, hemorrhagic shock, shock-like syndromes, capillary leak syndromes induced by immunotherapy of cancer, acute respiratory distress syndrome, traumatic shock, immune- and pathogen-induced pneumonias, immune complex-mediated pulmonary injury and chronic obstructive pulmonary disease, inflammatory bowel diseases (including ulcerative colitis, Crohn's disease and post-surgical trauma), gastrointestinal ulcers, diseases associated with ischemia-reperfusion injury (including acute myocardial ischemia and infarction, acute renal failure, ischemic bowel disease and acute hemorrhagic or ischemic stroke), immune-complex-mediated glomerulonephritis, autoimmune diseases (including insulin-dependent diabetes mellitus, multiple sclerosis, rheumatoid arthritis, osteoarthritis and systemic lupus erythematosus), acute and chronic organ transplant rejection, transplant arteriosclerosis and fibrosis, cardiovascular disorders (including hypertension, atherosclerosis, aneurysm, critical leg ischemia, peripheral arterial occlusive disease and Reynaud's syndrome), complications of diabetes (including diabetic nephropathy, neuropathy and retinopathy), ocular disorders (including macular degeneration and glaucoma), neurodegenerative disorders (including delayed neurodegeneration in stroke, Alzheimer's disease, Parkinson's disease, encephalitis and HIV dementia), inflammatory and neuropathic pain including arthritic pain, periodontal disease including gingivitis, ear infections, migraine, benign prostatic hyperplasia, cancers including, but not limited to, leukemias and lymphomas, prostate cancer, breast cancer, lung cancer, malignant melanoma, renal carcinoma, head and neck tumors and colorectal cancer.

The crystalline potassium salt of Formula (I) is also useful in treating folliculitis induced by inhibitors of epidermal growth factor (EGF) or epidermal growth factor receptor (EGFR) kinase used in the treatment of solid tumors. Clinical trials have revealed folliculitis (inflammation of the hair follicle manifested by severe acne-like skin rash on the face, chest and upper back) as a major dose-limiting side effect of such treatments. Such folliculitis is associated with an infiltration of neutrophils, suggesting products secreted by activated neutrophils to be the cause of the inflammation. The crystalline potassium salt of Formula (I) inhibits neutrophil- or eosinophil-mediated inflammation, and is therefore useful in treating such folliculitis, thereby improving the quality of life of the treated cancer patients but also allowing for the increase of the dosage of the EGF inhibitor or EGFR kinase inhibitor or the extension of the duration of the treatment, resulting in improved efficacy of the desired inhibitor.

The crystalline potassium salt of Formula (I) is also useful in the treatment of pulmonary and respiratory inflammation, including, but not limited to, asthma, chronic bronchitis, bronchiolitis, bronchiolitis obliterans (including such with organizing pneumonia), allergic inflammation of the respiratory tract (including rhinitis and sinusitis), eosinophilic granuloma, pneumonias, pulmonary fibroses, pulmonary manifestations of connective tissue diseases, acute or chronic lung injury, chronic obstructive pulmonary diseases, adult respiratory distress syndrome, and other non-infectious inflammatory disorders of the lung characterized by eosinophil infiltration. For example, the crystalline potassium salt of Formula (I) is useful in the inhibition of: eosinophil-mediated inflammation of the lung or tissues; neutrophil-mediated inflammation of the lung; lymphocyte-mediated inflammation of the lung; cytokine and chemokine production, including interleukin-5, interleukin-13 and eotaxin; lipid mediator generation, including prostaglandin $E_2$ and cysteinyl leukotrienes; airway hyper-responsiveness; and airway and vascular inflammation.

I. TESTING OF THE CRYSTALLINE POTASSIUM SALTS OF THE INVENTION

A hallmark of inflammation is the adhesion and transmigration across endothelium of neutrophils, eosinophils and other inflammatory cells. A similar process is observed for the migration of cells across polarized epithelial cells that occur in the lung, gastrointestinal tract and other organs. Cell culture models of these processes are available and have been used to show that lipoxin $A_4$ and stable lipoxin $A_4$ analogs inhibit the transmigration of human neutrophils across human endothelial cells and epithelial cells, including the human intestinal epithelial cell line $T_{84}$. Accordingly, one of ordinary skill in the art can test a crystalline potassium salt of Formula (I) for its ability to inhibit the transmigration of human neutrophils and eosinophils across human endothelial cells and epithelial cells by performing assays similar to those described in Colgan, S. P., et al., *J. Clin. Invest.* (1993), Vol. 92, No. 1, pp. 75-82; and Serhan, C. N., et al., *Biochemistry* (1995), Vol. 34, No. 44, pp. 14609-14615.

The air pouch model and/or the mouse zymosan-induced peritonitis model may be used to evaluate the in vivo efficacy of the crystalline potassium salt of Formula (I) in treating an inflammatory response. These are acute experimental models of inflammation characterized by infiltration of inflammatory cells into a localized area. See, e.g., the in vivo assays described in Ajuebor, M. N., et al., *Immunology* (1998), Vol. 95, pp. 625-630; Gronert, K., et al., *Am. J. Pathol.* (2001), Vol. 158, pp. 3-9; Pouliot, M., et al., *Biochemistry* (2000), Vol. 39. pp. 4761-4768; Clish, C. B., et al., *Proc. Natl. Acad. Sci. U.S.A.* (1999), Vol. 96, pp. 8247-8252; and Hachicha, M., et al., *J. Exp. Med.* (1999), Vol. 189, pp. 1923-30.

Animal models (i.e., in vivo assays) may also be utilized to determine the efficacy of the crystalline potassium salt of Formula (I) in treating asthma and related disorders of the pulmonary and respiratory tract. See, e.g., the assays described in De Sanctis, G. T. et al., *Journal of Clinical Investigation* (1999), Vol. 103, pp. 507-515; and Campbell, E. M., et al., *J. Immunol.* (1998), Vol. 161, No. 12, pp. 7047-7053.

Alternatively, a crystalline potassium salt of Formula (I) may be tested for its efficacy in the claimed methods of use by employing the assays described in U.S. Pat. No. 6,831,186 and in U.S. Patent Application Publication No. 2004/0162433, the pertinent disclosures of which are incorporated in full in their entireties herein.

J. ADMINISTRATION OF THE CRYSTALLINE POTASSIUM SALTS OF THE INVENTION

Administration of a crystalline salt of Formula (I), as a single stereoisomer or any mixture of stereoisomers, or as a cyclodextrin clathrate thereof, or as a solvate or polymorph, in pure form or in an appropriate pharmaceutical composition, can be carried out via any of the accepted modes of administration or agents for serving similar utilities. Thus, administration can be, for example, orally, nasally, parenterally, pulmonary, topically, transdermally, or rectally, in the form of solid, semi-solid, lyophilized powder, or liquid dosage forms, such as for example, tablets, suppositories, pills, soft elastic and hard gelatin capsules, powders, solutions, suspensions, aerosols, patches, or the like, preferably in unit dosage forms suitable for simple administration of precise dosages. The compositions will include a potassium salt of the invention as the/an active agent and a conventional pharmaceutical carrier or excipient and, in addition, may include other medicinal agents, pharmaceutical agents, carriers, adjuvants, etc., as are generally known in the art.

Actual methods of preparing such dosage forms are known, or will be apparent, to those skilled in this art; for example, see *Remington's Pharmaceutical Sciences*, 18th Ed., (Mack Publishing Company, Easton, Pa., 1990). The composition to be administered will, in any event, contain a therapeutically effective amount of a crystalline potassium salt of Formula (I) for treatment of a disease-state characterized by inflammation in accordance with the teachings of this invention.

Generally, depending on the intended mode of administration, the pharmaceutically acceptable compositions will contain about 0.1% to about 99.9% by weight of a crystalline potassium salt of Formula (I) and about 99.9% to about 0.1% by weight of a suitable pharmaceutical excipient.

In one embodiment, the route of administration is oral, using a convenient daily dosage regimen that can be adjusted according to the degree of severity of the disease-state to be treated. For such oral administration, a pharmaceutically acceptable composition containing the crystalline potassium salt of Formula (I) is formed by the incorporation of one or more of the normally employed pharmaceutically acceptable excipient(s). Such compositions take the form of solutions, suspensions, tablets, pills, capsules, powders, sustained release formulations and the like.

Preferably, such compositions will take the form of a capsule, caplet or tablet and therefore will also generally contain a diluent, a disintegrant, a lubricant, and a binder.

The crystalline potassium salt of Formula (I) may also be formulated into a suppository comprising the active ingredient disposed in a carrier that slowly dissolves within the body, such as those normally employed in this capacity.

Liquid pharmaceutically administrable compositions can, for example, be prepared by dissolving, dispersing, etc., a potassium salt of the invention and optional pharmaceutically acceptable adjuvants in a carrier, such as, for example, water, saline, aqueous dextrose, glycerol, ethanol and the like, to thereby form a solution or suspension.

If desired, a pharmaceutical composition of the invention may also contain minor amounts of auxiliary substances such as wetting or emulsifying agents, pH buffering agents, antioxidants, and the like.

The crystalline potassium salt of Formula (I) is administered in a therapeutically effective amount, which will vary depending upon a variety of factors including the activity of the specific compound employed; the metabolic stability and length of action of the crystalline potassium salt of Formula (I); the age, body weight, general health, sex, and diet of the patient; the mode and time of administration; the rate of excretion; the drug combination; the severity of the particular disease-state(s) to be treated; and the host undergoing therapy.

EXAMPLES

The following Examples further describe the preparation of the crystalline potassium salt of Formula (Ia). The crystalline potassium salts of other lipoxin $A_4$ analogs of Formula (I) may also be prepared analogously.

Example 1

Preparation of Monohydrate Form of the Crystalline Potassium Salt (Ia) by Crystallisation and Drying Under Conditions that Correlate with Stability Domain of the Monohydrate 2-((2S,3R,4E,6E,10E,12S)-13-(4-fluorophenoxy)-2,3,12-trihydroxytrideca-4,6,10-trien-8-ynyloxy)acetic acid (compound (IIa)) (964 g) was dissolved in a mixture of dry ethanol (3.850 L) and water (0.580 L). In a second flask, potassium hydroxide pellets (172.2 g) were dissolved in a mixture of water (0.580 L) and dry ethanol (3.850 L). The potassium hydroxide solution was added slowly to the solution of starting acid (IIa) at 20° C. until pH of 8.5 was measured using wet pH paper. Seed crystals (2.5 g) were added to the solution. After 90 minutes at 22° C., a seed bed formed and the suspension was cooled to −10° C. within 45 min and stirred at this temperature for an additional 2 hours. The cold suspension was then filtered using a suction filter with filter paper. The collected crystals were washed three times with 1.6 L of a cooled mixture of ethanol/water (−10° C.; 6.0% wt of water), and then dried to a constant mass at 200 mbar/30° C. in a vacuum-drying cabinet using air (relative humidity ~30%) as the sweep gas. The drying process was controlled by the determination of the water content (via Karl Fischer Titration) of several samples taken during the drying process. The crystalline monohydrate form of the potassium salt of Formula (Ia) (901 g) was obtained.

Example 2

Preparation of Monohydrate Form of the Crystalline Potassium Salt (Ia) by Drying Via a Microwave Dryer 2-((2S,3R,4E,6E,10E,12S)-13-(4-fluorophenoxy)-2,3,12-trihydroxytrideca-4,6,10-trien-8-ynyloxy)acetic acid (compound (IIa)) (50.05 g) was dissolved in a mixture of dry ethanol (158.11 g) and water (30.07 g). In a second flask, potassium hydroxide pellets (12.24 g) were dissolved in a mixture of water (41.22 g) and dry ethanol (216.15 g). The potassium hydroxide solution (180.21 g) was added slowly to the solution of starting acid (IIa) at 20° C. until pH of 8.5 was measured using wet pH paper. The solution was cooled down to 0° C. Seed crystals were suspended in ethanol and the resulting suspension (0.3 g) was added to the solution. After 30 min a seed bed formed and the suspension was cooled to −12° C. within 30 min and stirred at this temperature for an additional 1 hour. The cold suspension was then filtered using a suction filter with filter paper. The collected crystals were washed with 0.1 L of a cooled mixture of ethanol/water (−12° C.; 4.0% wt of water). A sample of the wet filterpad showed the dihydrate via using XRPD analysis. Then the drying process was started in a microwave dryer. Drying conditions: Power=80 W, pressure inside the dryer <150 mbar. After 3.7 hours drying time the mass of the crystals was constant and the crystalline monohydrate form of the potassium salt of Formula (Ia) (XRPD-Analysis, thermogravimetric analysis) (38.97 g) was obtained.

Example 3

Preparation of Dihydrate Form of the Crystalline Potassium Salt (Ia) by Crystallization and Drying Under Conditions that Correlate with the Stability Domain of the Dihydrate 2-((2S,3R,4E,6E,10E,12S)-13-(4-fluorophenoxy)-2,3,12-trihydroxytrideca-4,6,10-trien-8-ynyloxy)acetic acid (compound (IIa)) (500 mg) was dissolved in ethanol (2 mL). Water (0.75 mL) was added to the solution. The resulting clear solution was stirred. Potassium hydroxide pellets (85.3 mg) were dissolved in ethanol (2.84 mL). The resulting solution was clear and without a solid phase. An equimolar amount of the clear potassium hydroxide solution was added to the solution of starting acid (IIa). The dosage of the potassium hydroxide solution added was carried out by a pH check (wet pH-indicator strip). The addition of the potassium hydroxide solution was stopped when the solution reached a pH of 8.5. The stirred solution was cooled to −10° C. After 2 hours, a suspension was detectable. The suspension was stirred an additional hour. The suspension was centrifuged in a precooled centrifuge and the mother liquid was decanted. The solid phase was dried in a circulating air dryer at 30° C. The atmosphere of the circulating air dryer was conditioned to 70% relative humidity by sweep gas humidification. A sweep gas flow ($N_2$) was continuously introduced into the dryer. The sweep gas flow was alternately dry or moistened with water. The time periods of the moistened versus the dry $N_2$ flow were regulated via automatic control technology that considers the relative humidity inside the dryer. Using this technique, it was possible to guarantee a relative humidity of 70% inside the dryer during the storage period. The XRPD analysis of the wet filterpad as well as samples of the solid in the dryer after 8 hours and 32 hours (=dry product) drying time showed the crystalline dihydrate form of the potassium salt (Ia).

Example 4

Preparation of Dihydrate Form of the Crystalline Potassium Salt (Ia) from the Monohydrate Form by Storage Under Dihydrate Conditions The monohydrate form of the potassium salt (Ia) (1.697 g) was transferred into a dish. The monohydrate form of the substance at the beginning of the process was established by XRPD-analysis and thermogravimetric analysis. The mass of the sample taken was 127 mg. The dish was transferred into a circulating air dryer. The storage conditions were atmospheric pressure and 25° C. A moistened sweep gas flow ($N_2$) analogous to Example 2 was continuously introduced into the dryer. Using this technique, it was possible to guarantee a relative humidity of 70% inside the dryer during the storage period. The first sample (mass=239 mg) was taken after about 48 hours and represented the dihydrate form of the potassium salt (Ia) (XRPD analysis, thermogravimetric analysis). The second sample (mass=220 mg) was taken another 24 hours later. This sample of the stored substance also represented the dihydrate form (XRPD-Analysis, thermogravimetric analysis). The remaining mass inside the dish=1.168 g of the crystalline dihydrate form of the potassium salt (Ia).

Example 5

Preparation of Anhydrate Form of the Crystalline Potassium Salt (Ia) from the Monohydrate Form by Suspending in a Suitable Solvent The monohydrate form of the potassium salt (Ia) (12.42 g) was transferred into a flask. The monohydrate form of the substance was established by XRPD-analysis and thermogravimetric analysis. 1,4-Dioxane solvent (125 mL) were added to the flask, which was then closed by a flexible membrane. The suspension was agitated via a magnetic stirrer and heated up to 95° C. for 6 hours, after which the suspension was cooled down to approximately room temperature and the crystals were isolated from solution with a suction filter. The wet filtercake was washed with 50 mL solvent (1,4-dioxane, room temperature) and then dried in a vacuum-drying cabinet at 100 mbar and 40° C. After 44 hours drying time, 10.851 g of the crystalline anhydrate form of the potassium salt (Ia) (XRPD-Analysis, thermogravimetric analysis, residual solvent) was yielded.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A crystalline potassium salt of 2-((2S,3R,4E,6E,10E,12S)-13-(4-fluorophenoxy)-2,3,12-trihydroxytrideca-4,6,10-trien-8-ynyloxy)acetate:

which is in the form of an anhydrate characterized by a X-ray powder diffraction pattern having a characteristic peak at about d=26.7 Å;

in the form of an anhydrate characterized by a X-ray powder diffraction pattern having a characteristic peak at about d=26.7 Å and about d=3.7 Å;

in the form of a monohydrate characterized by a X-ray powder diffraction pattern having a characteristic peak at about d=26.5 Å;

is in the form of a monohydrate characterized by a X-ray powder diffraction pattern having a characteristic peak at about d=26.5 Å, about d=4.3 Å and about d=4.0 Å;

in the form of a dihydrate characterized by a X-ray powder diffraction pattern having a characteristic peak at about d=27.1 Å; or in the form of a dihydrate characterized by a X-ray powder diffraction pattern having a characteristic peak at about d=27.1 Å, about d=4.2 Å and about d=4.1 Å.

2. The crystalline potassium salt according to claim 1 wherein the crystalline potassium salt is in the form of an anhydrate characterized by a X-ray powder diffraction pattern having a characteristic peak at about d=26.7 Å.

3. The crystalline potassium salt according to claim 1 wherein the crystalline potassium salt is in the form of an anhydrate characterized by a X-ray powder diffraction pattern having a characteristic peak at about d=26.7 Å and about d=3.7 Å.

4. The crystalline potassium salt according to claim 1 wherein the crystalline potassium salt is in the form of a monohydrate characterized by a X-ray powder diffraction pattern having a characteristic peak at about d=26.5 Å.

5. The crystalline potassium salt according to claim 1 wherein the crystalline potassium salt is in the form of a monohydrate characterized by a X-ray powder diffraction pattern having a characteristic peak at about d=26.5 Å, about d=4.3 Å and about d=4.0 Å.

6. The crystalline potassium salt according to claim 1 wherein the crystalline potassium salt is in the form of a dihydrate characterized by a X-ray powder diffraction pattern having a characteristic peak at about d=27.1 Å.

7. The crystalline potassium salt according to claim 1 wherein the crystalline potassium salt is in the form of a dihydrate characterized by a X-ray powder diffraction pattern having a characteristic peak at about d=27.1 Å, about d=4.2 Å and about d=4.1 Å.

8. A pharmaceutical composition comprising one or more pharmaceutically acceptable excipient(s) and a therapeutically effective amount of a crystalline potassium salt of claim 1.

Figure 2:
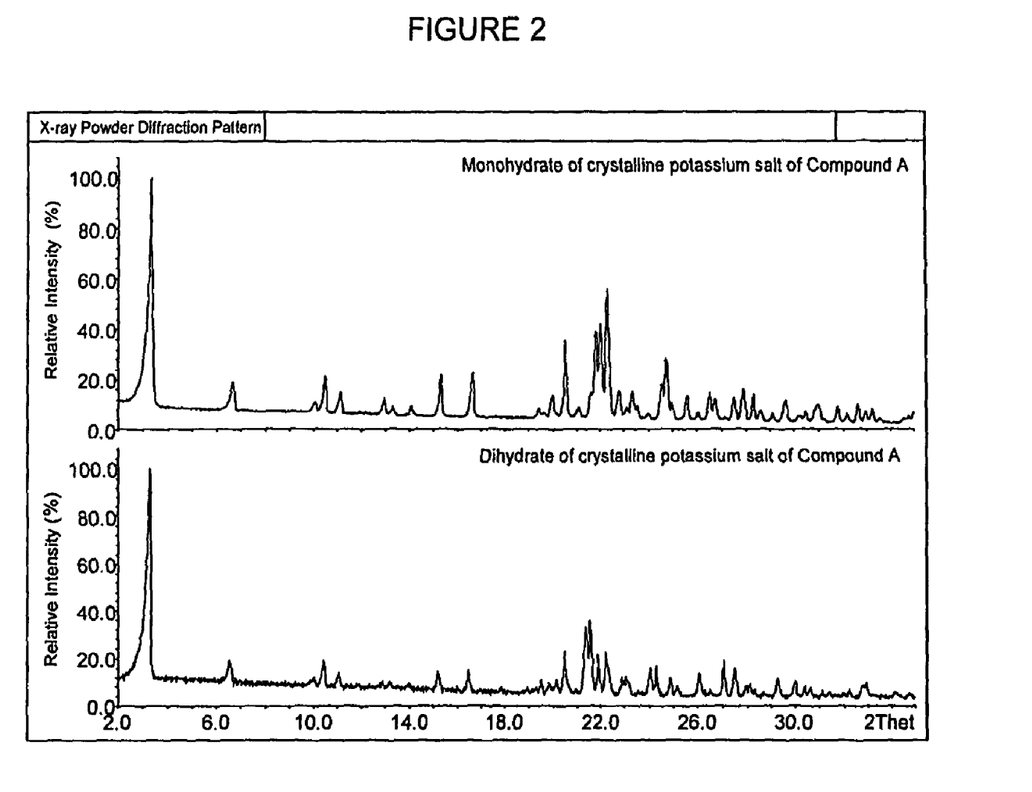
FIG. 2 illustrates X-ray diffraction patterns.
Figure 3:
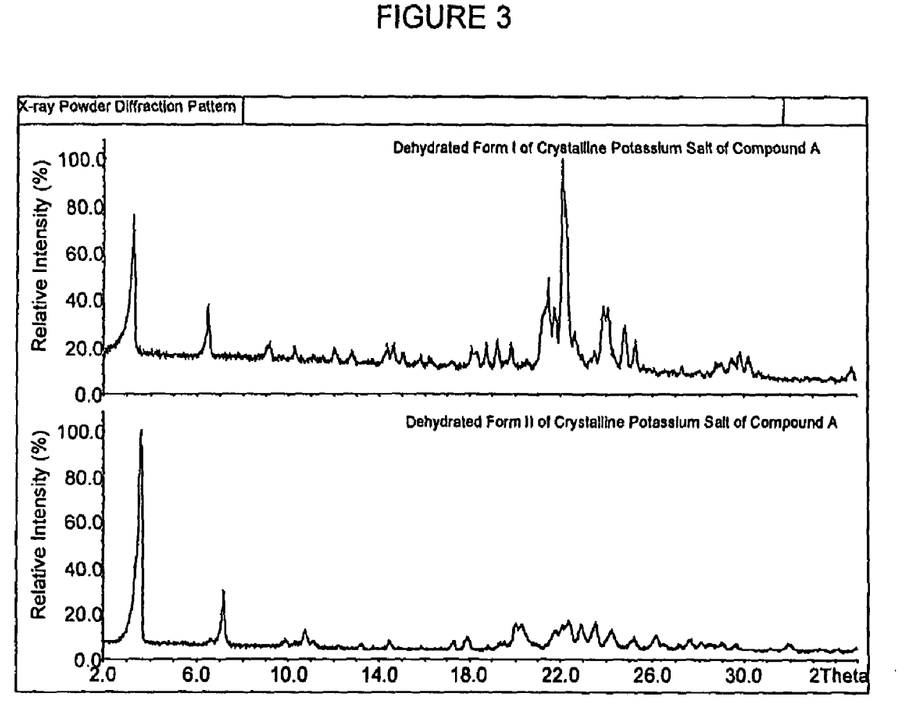
FIG. 3 illustrates X-ray diffraction patterns.

9. The crystalline potassium salt according to claim 1, wherein the crystalline potassium salt has the X-ray powder diffraction patterns illustrated in FIG. 2 and is a monohydrate.

10. The crystalline potassium salt according to claim 1, wherein the crystalline potassium salt has the X-ray powder diffraction patterns illustrated in FIG. 2 and is a dihydrate.

* * * * *